United States Patent [19]

Motola et al.

[11] Patent Number: 5,028,625

[45] Date of Patent: Jul. 2, 1991

[54] ACID ADDITION SALT OF IBUPROFEN AND MEGLUMINE

[75] Inventors: Solomon Motola, Marlton; Alan R. Branfman; Gary R. Agisim, both of Cherry Hill; Donald J. Quirk, Hammonton, all of N.J.

[73] Assignee: American Home Products Corporation, New York, N.Y.

[21] Appl. No.: 369,412

[22] Filed: Jun. 20, 1989

[51] Int. Cl.$^5$ ..................... A61K 31/19; A61K 31/14
[52] U.S. Cl. .................................. 514/557; 514/642; 424/464
[58] Field of Search ................................ 514/557, 642

[56] References Cited

U.S. PATENT DOCUMENTS 4,877,620  10/1989  Loew et al. ..................... 424/451

FOREIGN PATENT DOCUMENTS 63-146815  6/1988  Japan.
1527563  11/1976  United Kingdom.

*Primary Examiner*—C. Warren Ivy
*Assistant Examiner*—Celia Chang
*Attorney, Agent, or Firm*—John W. Routh

[57] ABSTRACT

A water-soluble salt of ibuprofen with meglumine (N-methylglucamine) is prepared, isolate and characterized and pharmaceutical preparations containing the salt for oral administration are described which are clear, pleasant tasting liquids.

1 Claim, No Drawings

ACID ADDITION SALT OF IBUPROFEN AND MEGLUMINE

This invention relates to the novel water soluble acid addition salt of meglumine with ibuprofen. More particularly, this invention relates to the acid addition salt of meglumine with ibuprofen having improved water solubility and waste and to palatable pharmaceutical compositions incorporating such salt, especially liquid preparations for oral administration.

BACKGROUND OF THE INVENTION

Ibuprofen is a non-steroidal anti-inflaxatory and analgesic drug (NSAID) which is sparingly soluble in water and has a characteristic bitter taste and associated aftertaste and pharyngeal irritation (throat bite). Meglumine salts of other NSAIDs are described in U.S. Pat. No. 4,748,174 issued May 31, 1988 as being water-soluble and suitable for use in liquid parenteral and oral pharmaceutical preparations. The disclosure of patent 4,748,174 is, therefore, incorporated herein by reference in its entirety. Pediatric ibuprofen formulations are disclosed in U.S. Pat. No. 4,788,220 issued Nov. 29, 1988 wherein finely divided ibuprofen is suspended in a liquid formulation with particular suspending and taste-masking agents. Such formulations are inherently limited in the amount of suspended ibuprofen per unit dose, i.e. five milliliters, due to the bitter taste of the ibuprofen and the large amount of suspending and taste-masking agents required.

SUMMARY OF THE INVENTION

It has now been found that meglumine, as the acid addition salt of ibuprofen, not only provides water solubility to the ibuprofen but also provides a significant taste-masking effect such that the meglumine acid addition salt of ibuprofen can be incorporated into palatable liquid formulations for oral administration. The acid addition salts are prepared by salifying the amino function of the meglumine with the carboxylic acid function of the ibuprofen in approximately equal molar amounts. Advantageously, the reaction medium is an organic solvent in which the ibuprofen and meglumine are mutually soluble, such as ethyl alcohol, wherein the ibuprofon is first dissolved and then the meglumine, with mixing, to form a clear solution. The clear solution can be concentrated, as by evaporation of the organic solvent, or the salt can be separated from the reaction medium such as by precipitation or crystallization, all as described in aforementioned U.S. Pat. No. 4,748,174. The clear solution concentrate containing, for example, about 740 milligrams per 10 milliliters, can be further dissolved in water to the desired dosage strength per 5 milliliters for oral administration, i.e. to a dosage strength 330 mg/5 ml or 300 mg/5 ml. The improved aqueous solubility and the improved taste of the ibuprofen meglumine salt thus permits the use of larger quantities of flavor enhancers and sweeteners, further to improve the taste characteristics of the orally administrable medicine.

DETAILED DESCRIPTION OF THE INVENTION

The meglumine salt of ibuprofen has been prepared and characterized by the procedures described in the following examples, wherein the ibuprofen, the meglumine and the ethyl alcohol were all of U.S.P. grade.

EXAMPLE 1

One hundred twenty grams (0.615 moles) of meglumine USP were dissolved in 700 grams of deionized water in a mixing vessel. One hundred twenty grams (0.582 moles) of ibuprofen USP were added to the meglumine solution and the mixture was stirred for one hour until a clear solution was observed. The clear solution indicated salt formation since the ibuprofen aqueous solubility (0.006% weight by volume) was well exceeded. The ibuprofenmeglumine molar ratio was 1:1.0566.

An additional 30 grams (0.145 moles) of ibuprofon was added to the clear solution and the batch was mixed vigorously for one hour. The resulting cloudy liquid was filtered to clarity through #40 Whatman filter paper to remove excess ituprofen and the resulting clear solution was stored at 5° C. for 6 days following which the liquid was filtered cold (5° C.) to clarity through #40 Whatman filter paper.

The filtered clear solution was subjected to lyophilization in a Virtis Freeze Dryer by first cooling the solution to $-50°$ C. and then heating over a four hour period to 30°–50° C. under a 25 millitorr vacuum. The residue was pulverized to a granular powder and the meglumine ibuprofen salt isolated as the granular powder was characterized as follows:

| | |
|---|---|
| Appearance: | Gray, granular amorphous deliguescent powder |
| Melting Point: | 53–55° C. |
| Moisture Content: | 0.7% |
| Ibuprofen Content: | 56% weight/weight |
| Water Solubility: | Extremely soluble |

The water solubility was determined by readily dissolving 129 grams of salt (containing 72.24 grams of ibupropen) in 100 milliliters of water to form a clear solution. Quantities greater than 129 grams of salt can be dissolved in 100 milliliters of water with an observable increase in viscosity. The solubility was confirmed by assay of a clear solution prepared from 10.32 grams of salt dissolved in 8 milliliters of water. Ibuprofen content: 31.05% w/w (98.45% of theoretical)

EXAMPLE 2

The meglumine ibuprofen salt of Example 1 can be used to prepare parenteral, rectal or topical dosage forms, as is well known in the art and described in aforementioned U.S. Pat. No. 4,748,174. To utilize the taste masking properties of the salt to best advantage, however, the salt is used to prepare dosage forms for oral adminstration, such as chewable tablets and liquid preparations for pediatric and geriatric patients.

Pleasant tasting clear liquid compositions can be prepared having the general formulation set forth below wherein the salt of Example 1 can be used or the salt can be made in situ during preparation of the formulation.

| Ingredient | Quantity % w/v |
|---|---|
| Ibuprofen, USP | 1–2 |
| Meglumine, USP | 1–2 |
| Polyethylene Glycol, NF | 15–25 |
| Propylene Glycol, USP | 0–5 |
| Ethyl Alcohol, USP | 5–15 |
| Glycerin, USP | 5–15 |
| Sorbitol Solution, USP | 5–15 |

| Ingredient | Quantity % w/v |
|---|---|
| Sucrose, NF | 30–70 |
| Sodium Saccharin, USP | 0–0.25 |
| Flavors | 0.05–1.0 |
| Citric Acid Hydrous, USP | 0–1.0 |
| Purified Water Deionized, USP | 30–40 |

In the above formulation, the ibuprofen is incorporated at 2% w/v to provide a 100 mg/5 ml dose. The meglumine is incorporated at a quantity approximately equimolar to that of the ibuprofen to form the meglumine ibuprofen salt.

The polyethylene glycol, propylene glycol and alcohol are secondary solubilizers for any free ibuprofen present after pH adjustment.

The glycerin serves as a bodying-sweetening agent, the sucrose and sorbitol are taste-masking/sweetening agents and the sodium saccharin is a sweetening agent.

The citric acid is added to adjust the pH to 6.7–7.0 and as a buffer and flavor enhancer. The adjustment of the pH to the 6.7–7.0 range eliminates any alkaline or soapy taste.

EXAMPLE 3

An actual formulation of the invention and within the scope of the formulation range of Example 2 is illustrated in this example.

| Ingredient | Quantity g/liter | Quantity % w/v |
|---|---|---|
| Ibuprofen, USP | 20.00 | 2.00 |
| Meglumine, USP | 20.00 | 2.00 |
| Alcohol, USP | 70.00 | 7.00 |
| Polyethylene Glycol 1450, NF | 200.00 | 20.00 |
| Propylene Glycol, USP | 50.00 | 5.00 |
| Glycerin, USP | 50.00 | 5.00 |
| Sorbitol Solution, USP | 100.00 | 10.00 |
| Sucrose, NF | 350.00 | 35.00 |
| Citric Acid Hydrous, USP | 0.57 | 0.057 |
| Sodium Saccharin, USP | 2.50 | 0.25 |
| Artificial flavor | 7.00 | 0.70 |
| Blue FDC 1 | 0.0015 | 0.00015 |
| Red FDC 40 | 0.47 | 0.047 |
| Purified Water, Deionized, USP | qs to 1 liter | qs to 100 ml |

This formulation provides a pleasant tasting, clear liquid composition having a wild cherry flavor in which the characteristic ibuprofen bitter taste and throat bite are masked. The product exhibits a pH of 6.77, a specific gravity of 1.19 and a viscosity of 75 cps when measured with a Brookfield RVF viscometer at 25° C. with Spindle #1 at 20 rpm. The ibuprofen content of 2.00% w/v (100 mg/5 ml dose) was confirmed by assay. The composition was physically and chemically stable after storage for one month at temperatures ranging from −5° to 45° C. as determined by observation and assay.

The procedure for preparing this formulation was step-wise as follows:

Step 1—The polyethylene glycol was heated until completely melted to a clear liquid at which time there were separately added and dissolved the ibuprofen, propylene glycol and a 70 gram portion of purified water. The batch was allowed to cool to 25–30° C. with mixing.

Step 2—The meglumine is dissolved in a 40 gram portion of purified water in a separate container and the sucrose is separately dissolved in a 175 gram heated portion of purified water and then cooled to 25°–30° C.

Step 3—To the main batch of step 1 were added in order, the alcohol, the meglumine solution, the glycerin, the sorbitol solution, the sucrose solution, the sodium saccharide, the flavor and the dyes, the latter three also as solutions in purified water.

Step 4—A sufficient quantity of citric acid in purified water solution is added to adjust the pH to 6.7–7.0 and then the remaining purified water is added qs to one liter.

| Ingredient | Quantity g/liter | Quantity % w/v |
|---|---|---|
| Ibuprofen, USP | 20.00 | 2.00* |
| Meglumine, USP | 20.00 | 2.00 |
| Alcohol, USP | 150.00 | 15.00** |
| Sucrose, NF | 660.00 | 66.00 |
| Citric Acid Hydrous, USP | 0.90 | 0.09 |
| Artificial Flavor | 7.00 | 0.70 |
| Purified Water, Deionized, USP, | qs to 1 Liter | qs to 100 ml |

*2% w/v ibuprofen is equivalent to 100 mg/5 ml dose
**15 w/v Alcohol, USP is equivalent to 17.65% v/v anhyrous ethyl alcohol The procedure for preparing this formulation was stepwise as follows:

Step 1—A 330 gram portion of the purified water was heated to 70–75° C., the sucrose was added and dissolved therein and the solution was cooled to 25–30° C.

Step 2—The ibuprofen is dissolved in the alcohol in a separate container, the meglumine is separately dissolved in 40 grams of the purified water, the meglumine solution is added to the ibuprofen solution, and the combined ibuprofen-meglumine solution is added to the main batch.

Step 3—In a separate container the citric acid is dissolved in purified water.

Step 4—To the main batch are added stepwise the flavor, sufficient citric acid to adjust the pH to 6.7–7.0 and sufficient purified water is added to adjust the volume to one liter.

This formulation also provides a pleasant tasting, clear liquid composition having a wild cherry flavor in which the characteristic ibuprofen bitter taste and throat bite are masked. The liquid is slightly viscous with a specific gravity of 1.23 and a pH of 6.72.

EXAMPLE 5

In order to demonstrate the important solubilizing function of the meglumine, the procedure of Example 3 was carried out except that the meglumine and the citric acid were omitted. Step 1 was carried out and the sucrose dissolution in step 2 was accomplished. During step 3, the addition of the sucrose solution to the ibuprofen solution, the ibuprofer began to precipitate after the addition of only 38% (200 grams of the required 525 grams for a 1 liter batch) of the sucrose solution. After completion of steps 3 and 4, the product was filtered to clarity through #40 Whatman filler paper and found of assay to contain only 0.4% w/v (20mg/5ml) ibuprofen.

EXAMPLE 6

In order to demonstrate the important taste-masking function of the meglumine, the procedure of Example 3 was carried out except that the meglumine and citric acid were omitted and the levels of alcohol and glycols were increased proportionately at the expense of the sucrose to solubilize the iboprofen and maintain that solubility over a −5 to +45 C. temperature range. The product assayed 2% w/v (100 mg/5 ml) ibuprofen and had the following formulation:

| Ingredient | Quantity % w/v | Quantity g/liter |
|---|---|---|
| Ibuprofen, USP | 2.00 | 20.00 |
| Alcohol, USP | 15.00* | 150.00 |
| Polyethylene Glycol 1450, NF | 30.00 | 300.00 |
| Propylene Glycol, USP | 8.00 | 80.00 |
| Glycerin, USP | 5.00 | 50.00 |
| Sorbitol Solution, USP | 10.00 | 100.00 |
| Sucrose, NF | 17.93 | 179.30 |
| Sodium Saccharin, USP | 0.25 | 2.50 |
| Artificial Flavor | 0.70 | 7.00 |
| Blue FDC 1 | 0.00015 | 0.0015 |
| Red FDC 40 | 0.047 | 0.47 |
| Purified Water, Deionized, USP | qs to 100 ml | qs to 1 liter |

*15.00% w/v Alcohol, USP is equivalent to 17.65% v/v, anhydrous ethyl alcohol.

Other than the omission of meglumine and citric acid this formulation is qualitatively identical to the formulation of Example 3 except that the glycol/alcohol content is the approximate minimum necessary and the sucrose content is the approximate maximum allowable level to assure a 2% w/v ibuprofen solubility over extended storage.

Ten persons (5 men and 5 women) comprised a tas&e panel and participated in a double blind taste test of the forxulations of Examples 3 and 6. All participants described the formulation of Example 3 as pleasant tasting and described the formulation of Example 6 as poor tasting with a pronounced ibuprofen bitter taste and throat bite.

In the preparation of the pleasant tasting liquid formulations for oral administration of the invention, water is the primary solubilizer for the meglumine ibuprofen salt and alcohol and/or glycol are provided as a secondary solubilizer for any free ibuprofen present. Advantageously, a slight excess of meglumine over the molar equivalent of ibuprofen is used so that no free ibuprofen is present in the aqueous base formulation. Also, the primary taste-masking agent is meglumine to eliminate the bitter taste and throat-bite, while sucrose and/or sorbitol are the secondary taste-masking agents. Other ingredients can be added, for example, to form a complex with the ibuprofen, such as polyvinylpyrrolidone as described in U.S. Pat. No. 4,704,436 issued Nov. 3, 1987, so as to remove any excess ibuprofen from solution.

A significant advantage of the use of the meglumine ibuprofen salt, in addition to its taste masking effect, is its high solubility in water which permits liquid preparations of increased therapeutic activity. Thus stable liquid preparations can be formulated having an ibuprofen content as high as 200 mg/5 ml which provide a dose equal to that of the commercial ADVIL tablets containing 200 mg of ibuprofen per tablet. Hence pediatric formulations containing 100 mg/5 ml can be prepared as well as adult or geriatric formulations containing 200 mg/5 ml.

EXAMPLE 7

The meglumine salt of ibuprofen was formed by dissolving 10 grams of Ibuprofen, USP, in 330 milliliters of Alcohol, USP to which was added 10 grams of Meglumine, USP. The ibuprofen-meglumine molar ratio was 1:1.0566. The batch was stirred until a clear solution was observed indicating that the meglumine ibuprofen salt had formed since the meglumine alcohol solubility limit (1.2 grams in 100 ml) had been exceeded.

A 10 milliliter portion of the solution was withdrawn and subjected to evaporation conditions under a continuous air current until a clear viscous liquid was obtained weighing 740 milligrams. The 740 milligrams of residue was redissolved in 7.5 milliliters of water to provide a clear solution containing approximately 4% w/v (200 mg/5ml) of therapeutically active ibuprofen "as the meglumine salt." The solution was clear with a pH of 8.35 and a slightly alkaline or soapy taste.

Hence, the concentration of therapeutically active ibuprofen in the liquid pharmaceutical preparations for oral administration of this invention can range from about 80 or 100 mg/5nl to about 200 mg/5ml.

A clear solution of an equivalent quantity (4% w/v) of free ibuprofen in an aqueous alcohol/glycol media was prepared. The 4% w/v ibuprofen solution as the meglumine ibuprofen salt exhibited significantly less of the characteristic unpleasant ibuprofen taste and throat bite than was observed with the 4% w/v alcohol/glycol solution.

We claim:

1. A solid palatable pharmaceutical chewable tablet for oral administration comprising the acid addition salt of meglumine and ibuprofen and a pharmaceutically acceptable carrier therefor.

* * * * *